United States Patent
Lim et al.

(10) Patent No.: US 9,969,735 B2
(45) Date of Patent: May 15, 2018

(54) PROCESS FOR MAKING TRICYCLIC LACTAM COMPOUNDS

(71) Applicant: Genentech, Inc., South San Francisco, CA (US)

(72) Inventors: Ngiap-Kie Lim, South San Francisco, CA (US); Haiming Zhang, San Mateo, CA (US); Chong Han, Foster City, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days. days.

(21) Appl. No.: 15/652,776

(22) Filed: Jul. 18, 2017

(65) Prior Publication Data

US 2017/0313704 A1 Nov. 2, 2017

Related U.S. Application Data

(63) Continuation of application No. PCT/EP2015/074352, filed on Oct. 21, 2015.

(60) Provisional application No. 62/069,176, filed on Oct. 27, 2014.

(51) Int. Cl.
C07D 471/14 (2006.01)

(52) U.S. Cl.
CPC ................... *C07D 471/14* (2013.01)

(58) Field of Classification Search
CPC .................................... C07D 471/14
USPC ........................................... 546/86
See application file for complete search history.

(56) References Cited

U.S. PATENT DOCUMENTS

| | | | |
|---|---|---|---|
| 7,514,444 B2 | 4/2009 | Honigberg et al. |
| 8,618,107 B2 | 12/2013 | Barbosa et al. |
| 8,716,274 B2 | 5/2014 | Crawford et al. |
| 8,722,676 B2 | 5/2014 | Crawford et al. |
| 8,729,072 B2 | 5/2014 | Crawford et al. |

FOREIGN PATENT DOCUMENTS

| | | |
|---|---|---|
| WO | 2011/140488 A1 | 10/2011 |
| WO | 2013/067260 | 5/2013 |
| WO | 2013/067274 A1 | 10/2013 |

OTHER PUBLICATIONS

Singlr step synthesis of 5,6,7,8-tetrahydroindolizines via Annulation of 2-Formylpiperidine and 1,3-dicarbonyl compounds Simone Capomolla 2015.*

Feldhahn et al., "Mimicry of a constitutively active pre-B cell receptor in acute lymphoblastic leukemia cells" The Journal of Experimental Medicine 201(11): 1837-1852 (Jun. 2005).
Liu et al., "Antiarthritis Effect of a Novel Bruton's Tyrosine Kinase (BTK) Inhibitor in Rat Collagen-Induced Arthritis and Mechanism-Based Pharmacokinetic/Pharmacodynamic Modeling: Relationships between Inhibition of BTK Phosphorylation and Efficacy" The Journal of Pharmacology and Experimental Therapeutics 338(1):154-163 (Mar. 2011)
Hunter et al., "A Thousand and One Protein Kinases" Molecular Biology and Virology Laboratory 50:823-829 (Sep. 1967).
Liu et al., "Significant Species Difference in Amide Hydrolysis of GDC-0834, a Novel Potent and Selective Bruton's Tyrosine Kinase Inhibitor" Drug Metabolism and Disposition 39(10): 1840-1849 (May 2011).
Xu et al., "RN486, a Selective Bruton's Tyrosine Kinase Inhibitor, Abrogates Immune Hypersensitivity Responses and Arthritis in Rodents" The Journal of Pharmacology and Experimental Therapeutics 341(1):91-103 (Sep. 2011).
Lou et al., "Bruton's Tyrosine Kinase Inhibitors: Approaches to Potent and Selective Inhibition, Preclinical and Clinical Evaluation for Inflammatory Diseases and B Cell Malignancies" Journal of Medicinal Chemistry 55:45394550 ( 2012).
Smith et al., "'Constrained analogs of CB-1 antagonists: 1, 5, 6, 7-Tetrahydro-4H-pyrrolo[3,2-c] pyridine-4-one derivatives'" Bioorganic & Medicinal Chemistry Letters 17 (3):673-678 (Jan. 19, 2007).
Kim et al., "Imidazo[1,5-a] quinoxalines as irreversible BTK inhibitors for the treatment of rheumatoid arthritis" Bioorganic & Medicinal Chemistry Letters 21:62586263 ( 2011).
Di Paolo et al., "Specific Btk inhibition suppresses B cell- and myeloid cell-mediated arthritis" Nature Chemical Biology 7:41-50 (Jan. 2011).
Islam et al., "The cellular phenotype conditions Btk for cell survival or apoptosis signaling" Immunological Reviews 178:49-63 ( 2000).
Simona S. Capomolla et al., "Single-Step Synthesis of 5,6,7,8-Tetrahydroindolizines via Annulation of 2-Formylpiperidine and 1,3-Dicarbonyl Compounds" Organic Letters 17:3564-3567 ( 2015).
Whang et al., "Bruton's tyrosine kinase inhibitors for the treatment of rheumatoid arthritis" Drug Discovery Today 19(8):1200-1204 (Aug. 2014).

* cited by examiner

*Primary Examiner* — Rita J Desai
(74) *Attorney, Agent, or Firm* — Mark D. Kafka; Genentech, Inc.

(57) ABSTRACT

Processes are described for the preparation of tricyclic lactam compound of Formula (I), having the structure and intermediates useful for the preparation of (I).

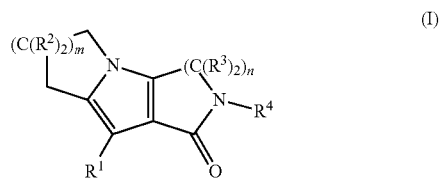

15 Claims, No Drawings

PROCESS FOR MAKING TRICYCLIC LACTAM COMPOUNDS

FIELD OF THE INVENTION

The invention relates to methods of making tricyclic lactam compounds, useful intermediates for preparing compounds for treating disorders mediated by Bruton's Tyrosine Kinase (Btk, BTK) including inflammation, immunological, and cancer, and more specifically to compounds which inhibit Btk activity.

BACKGROUND OF THE INVENTION

Bruton's Tyrosine Kinase (Btk) is a member of the Tec family of tyrosine kinases, and is a regulator of early B-cell development as well as mature B-cell activation, signaling, and survival (T. Hunter, Cell 1987 50:823-829). Inhibition of Btk activity can be useful for the treatment of allergic disorders and/or autoimmune and/or inflammatory diseases such as: SLE, rheumatoid arthritis (Whang et al (2014) Drug Discovery Today 19(8):1200-1204; Kim et al (2011) Bioorganic & Med. Chem. Letters 21:6258-6263), multiple vasculitides, idiopathic thrombocytopenic purpura (ITP), myasthenia gravis, allergic rhinitis, and asthma (Di Paolo et al (2011) Nature Chem. Biol. 7(1):41-50; Liu (2011) Drug Metab. and Disposition 39(10):1840-1849; Liu et al (2011) Jour. of Pharm. and Exper. Ther. 338(1):154-163; Lou et al (2012) J. Med. Chem. 55(10):4539-4550; Xu D. et al (2012) Jour. Pharm. and Exp. Ther. 341(1):90-103). In addition, Btk has been reported to play a role in apoptosis (Islam and Smith *Immunol. Rev.* 2000 178:49); thus, inhibition of Btk activity can be useful for cancer, as well as the treatment of B-cell lymphoma, leukemia, and other hematological malignancies (U.S. Pat. No. 7,514,444; Feldhahn et al. *J. Exp. Med.* 2005 201:1837).

Certain Btk-modulating compounds possess a tricyclic lactam substructural motif (U.S. Pat. No. 8,618,107; U.S. Pat. No. 8,729,072; U.S. Pat. No. 8,716,274; U.S. Pat. No. 8,722,676). The tricyclic lactam group of these compounds binds in the "H3 binding pocket". Modification of groups that bind in the H3 pocket can impart selective Btk modulating effects.

As reported by Di Paolo et al (2011) Nature Chem. Biol. 7(1):41-50, "this binding event induces a conformational change in Btk relative to the Apo structure (pdb 3P08) resulting in a Src-like inactive conformation of the kinase domain. This includes rearrangement of Y551 by ~18 Å from an extended, solvent exposed position to a buried conformation." This rearrangement and the inability for other kinases to adopt this confirmation imparts selectivity to certain Btk inhibitors.

SUMMARY OF THE INVENTION

The invention relates to methods of making tricyclic lactam compounds of Formula I, having the structure:

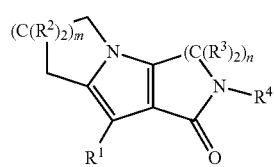

and stereoisomers, geometric isomers, tautomers, and pharmaceutically acceptable salts thereof. The various substituents are defined herein.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

Definitions

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically-labeled forms of the compounds. Isotopically-labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically-labeled compounds of the present invention, for example those into which radioactive or stable isotopes such as 3H, 13C, and 14C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of Formula I. The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Preparation of Tricyclic Lactam Compounds

The present invention includes processes, methods, reagents, and intermediates for the synthesis of tricyclic lactam compounds of Formula I.

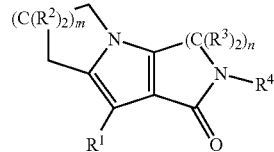

I

An exemplary Formula I compound is 3,4,6,7,8,9-hexahydropyrido[3,4-b]indolizin-1(2H)-one (CAS Reg. No. 1346672-96-5), useful for preparing BTK inhibitors, and which has the structure:

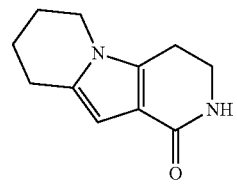 [SMILES: O=C1NCCc2c1cc1n2CCCC1]

Preparation of 3,4,6,7,8,9-hexahydropyrido[3,4-b]indolizin-1(2H)-one is described in U.S. Pat. No. 8,618,107 (compound 118d, FIG. 5); U.S. Pat. No. 8,729,072 (compound 101g, FIG. 1); U.S. Pat. No. 8,716,274 (compound 112d, FIG. 12); and U.S. Pat. No. 8,722,676 (compound 120d), which are expressly incorporated by reference.

Tricyclic lactam compounds of Formula I and intermediates for its preparation include all stereoisomers, geometric isomers, tautomers, and pharmaceutically acceptable salts thereof.

Tricyclic lactam compounds of Formula I may be prepared by cyclization of 2-carbonyl cyclic amine compound 1 and 1,3 keto-lactam compound 2.

An aspect of the invention is a process for preparing a tricyclic lactam compound of Formula I, having the structure:

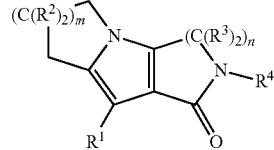

I comprising reacting intermediates 1 and 2 to form I

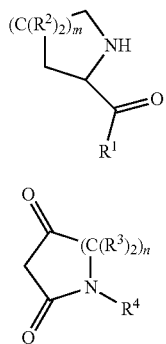

wherein $R^1$ is selected from H and $C_1$-$C_6$ alkyl;
$R^2$ is independently selected from H, F, Cl, $C_1$-$C_6$ alkyl, or phenyl;
$R^3$ are independently selected from H, F, Cl, $C_1$-$C_6$ alkyl, or phenyl;
$R^4$ is selected from H, tert-butyloxycarbonyl (Boc), benzyloxycarbonyl (CBz), allyloxycarbonyl (Alloc), or fluorenylmethyloxycarbonyl (Fmoc);
m is 1 or 2; and
n is 1 or 2, or 4,
where the tricyclic lactam compound of Formula I and intermediates 1 and 2 include all stereoisomers, geometric isomers, tautomers, and salts thereof.

In an exemplary embodiment, intermediate 1 is prepared by oxidation of alcohol intermediate 3:

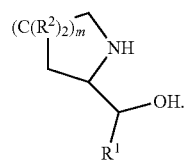

In an exemplary embodiment, intermediate 1 is prepared by a process comprising:
(a) reacting alcohol 3 with a protection reagent to form N-protected intermediate 4

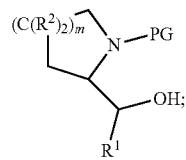

(b) oxidation of 4 to form oxidized N-protected intermediate 5

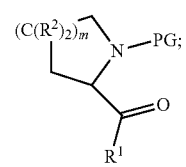

and
(c) deprotection of 5 to form 1,
where PG is tert-butyloxycarbonyl (Boc), benzyloxycarbonyl (CBz), allyloxycarbonyl (Alloc), or fluorenylmethyloxycarbonyl (Fmoc).

In an exemplary embodiment, PG is tert-butyloxycarbonyl (Boc).

In an exemplary embodiment, $R^1$ is H.

In an exemplary embodiment, $R^4$ is tert-butyloxycarbonyl (Boc).

In an exemplary embodiment, m is 1.

In an exemplary embodiment, m is 2.

In an exemplary embodiment, m is 2, n is 2, and each $R^2$ and $R^3$ is H.

In an exemplary embodiment, intermediate 1 is a salt.

In an exemplary embodiment, the process further comprises adding pyrrolidine to the reaction of intermediates 1 and 2.

In an exemplary embodiment, the process further comprises adding trifluoroacetic acid after the reaction of intermediates 1 and 2 whereby the tricyclic lactam compound of Formula I where $R^4$ is H is formed.

In an exemplary embodiment, intermediate 1 is piperidine-2-carbaldehyde hydrochloride.

In an exemplary embodiment, intermediate 2 is tert-butyl 2,4-dioxopiperidine-1-carboxylate.

In an exemplary embodiment, the tricyclic lactam compound of Formula I is 3,4,6,7,8,9-hexahydropyrido[3,4-b]indolizin-1(2H)-one.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In addition, the present invention embraces all geometric and positional isomers. In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the invention may exist in unsolvated as well as solvated forms with pharmaceutically acceptable solvents such as water, ethanol, and the like, and it is intended that the invention embrace both solvated and unsolvated forms.

The compounds of the invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The compounds of the invention also include isotopically-labeled compounds which are identical to those recited herein, but for the fact that one or more atoms are replaced by an atom having an atomic mass or mass number different from the atomic mass or mass number usually found in nature.

The invention relates to methods of making tricyclic lactam compounds, useful intermediates for preparing compounds for treating disorders mediated by Bruton's Tyrosine Kinase (Btk, BTK) including inflammation, immunological, and cancer, and more specifically to compounds which inhibit Btk activity. The compounds prepared include, but are not limited to, the compounds of the applications WO 2011/140488, WO 2013/067274 and WO 2013/067277 which are incorporated by reference. The process of the present invention is an improvement over earlier methods used in the prior art because it provides a higher yield in a more cost-effective manner using less expensive reagents for commercial scale production.

Starting materials and reagents for the preparation of the compounds of the invention are generally available from commercial sources such as Sigma-Aldrich Chemical (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

The following Schemes 1 and 2 illustrate the chemical reactions, processes, methodology for the synthesis of Formula I compounds, and certain intermediates and reagents.

Scheme 1:

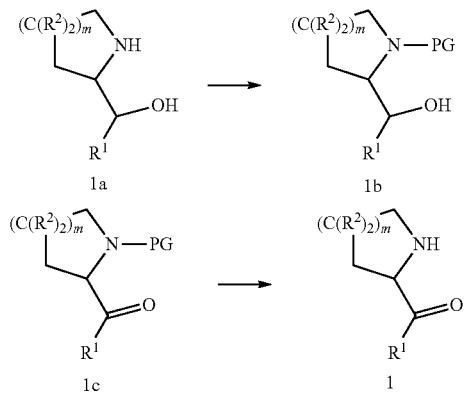

Scheme 1 shows the synthesis of intermediate 1 starting from alcohol 1a. $R^1$ is selected from H and $C_1$-$C_6$ alkyl; $R^2$ is independently selected from H, F, Cl, $C_1$-$C_6$ alkyl, or phenyl; and m is 1 or 2. Protection of the amine of 1a gives amine-protected alcohol 1b. Protecting groups (PG) include tert-butyloxycarbonyl (Boc), benzyloxycarbonyl (CBz), allyloxycarbonyl (Alloc), and fluorenylmethyloxycarbonyl (Fmoc). Oxidation of 1b gives amine-protected ketone 1c. Deprotection of 1c gives intermediate 1, including salt forms such as a hydrochloride salt. Salt forms may have advantages such as ease of handling, purification, separation of by-products, and stability. Exemplary intermediates 1 include:

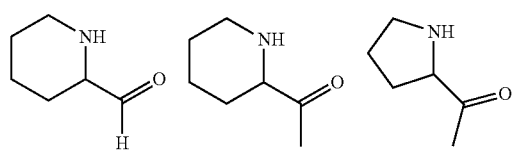

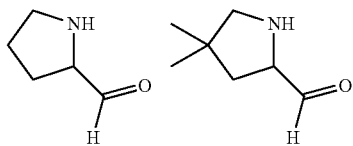

Scheme 2:

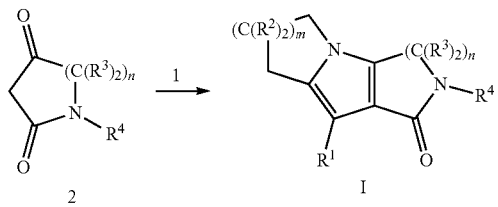

Scheme 2 shows the synthesis of tricyclic lactam compounds of Formula I by cyclization of intermediates 1 and 2. $R^1$ is selected from H and $C_1$-$C_6$ alkyl; $R^2$ is independently selected from H, F, Cl, $C_1$-$C_6$ alkyl, or phenyl; $R^3$ are independently selected from H, F, Cl, $C_1$-$C_6$ alkyl, or phenyl; $R^4$ is selected from H, tert-butyloxycarbonyl (Boc), benzyloxycarbonyl (CBz), allyloxycarbonyl (Alloc), or fluorenylmethyloxycarbonyl (Fmoc); m is 1 or 2; and n is 1 or 2. The amine of 2 may be protected as Boc, CBz, Alloc or Fmoc and removed after cyclization to form I where $R^4$ is H. The cyclization of 1 and 2 may be conducted in the presence of a secondary amine reagent, such as pyrrolidine, piperidine, or morpholine. The cyclization may proceed with the formation of a Schiff-base or enamine intermediate of 2 which reacts with 1. Where $R^4$ of 1 is Boc, the Boc group may be removed by treatment of the cyclization product I with an acidic reagent such as trifluoroacetic, trichloroacetic acid, or acetic acid to form the unprotected tricyclic lactam I where $R^4$ is H.

Exemplary intermediates 2 include:

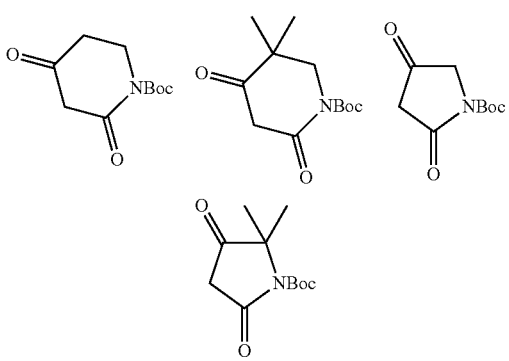

EXAMPLES

Example 1 tert-butyl 2-(hydroxymethyl)piperidine-1-carboxylate

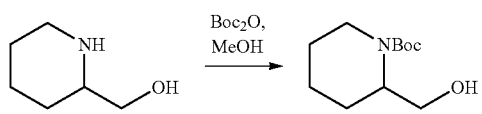 [SMILES: OCC1CCCCN1 ; CC(C)(C)OC(=O)N1CCCCC1CO]

Piperidin-2-ylmethanol (2.5 kg, 21.7 mol) was dissolved in MeOH (12.5 L). Di-tert-butyl dicarbonate (CAS Reg. No. 24424-99-5, Sigma-Aldrich #205249, Boc$_2$O, 3.8 kg, 21.7 mol) was added dropwise at 0~5° C. for 1 h. The mixture was warmed to 20~25° C. and stirred at this temperature for 16 h. After reaction completely, the mixture was concentrated under vacuum. The residue was dissolved in dichloromethane (DCM, 12.5 L) and washed with 1 N HCl (12.5 L) and 7% NaHCO$_3$ (12.5 L). The solution was concentrated under vacuum. The resulting residue, tert-butyl 2-(hydroxymethyl)piperidine-1-carboxylate, was obtained (8.61 kg) in 92% yield and used to next step without further purification. Characterization data was consistent with Molander, G. A. (2005) Tetrahedron, 61:2631-2643: $^1$H-NMR (400 MHz, CDCl$_3$) δ ppm 4.22-4.35 (m, 1H), 3.86-4.01 (m, 1H), 3.72-3.85 (m, 1H), 3.55-3.66 (m, 1H), 2.86 (br t, J=12.2, 1H), 2.42 (br s, 1H), 1.65-1.79 (m, 1H), 1.53-1.65 (m, 4H), 1.36-1.52 (m, 1H), 1.46 (s, 9H); $^{13}$C NMR (100 MHz, CDCl3) δ ppm 156.2, 79.7, 61.5, 52.5, 39.9, 28.4, 25.2, 25.1, 19.5; IR (neat): 3204, 3016, 2926, 1694, 1472 cm$^{-1}$.

Example 2 tert-butyl 2-formylpiperidine-1-carboxylate

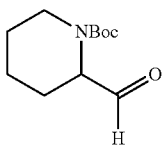 [SMILES: CC(C)(C)OC(=O)N1CCCCC1C=O]

Tert-butyl 2-(hydroxymethyl)piperidine-1-carboxylate (1.0 kg, 4.6 mol), 2,2,6,6-Tetramethyl-1-piperidinyloxy, free radical, 2,2,6,6-Tetramethylpiperidine 1-oxyl (TEMPO, Sigma-Aldrich #214000, CAS Reg No. 2564-83-2, Geisslmeir, David; et al. (2005) Monatsh. Chem 136(9), 1591-1599, 1.45 g, 9.29 mmol), NaBr (48 g, 0.46 mol) and NaHCO$_3$ (0.98 kg, 11.6 mol) in H$_2$O (5 L) and DCM (5 L) were cooled to 0~5° C. 10% NaOCl (6.22 kg, 8.36 mol) was added dropwise at 0~5° C. After addition, the mixture was stirred at 0~5° C. for 30 min. After reaction completed, the organic layer was separated and charged into another Reactor. 10% Na$_2$SO$_3$ was added dropwise to the organic layer to KI-starch paper indicating negative. The organic layer was separated, filtered, washed with H$_2$O and brine and dried over Na$_2$SO$_4$. The solvent was removed under vacuum. 0.8 kg of tert-butyl 2-formylpiperidine-1-carboxylate was obtained as an orange oil. (Assay Yield 80%). $^1$H NMR (400 MHz, CDCl$_3$) δ ppm 9.59 (br s, 1H), 4.38-4.71 (m, 1H), 3.78-4.10 (brm, 1H), 2.73-3.82 (brm, 1H), 2.11-2.21 (m, 1H), 1.57-1.71 (m, 3H), 1.30-1.71 (m, 10H), 1.26 (brs, 1H); 13C NMR (100 MHz, CDCl3) δ ppm 201.3, 158.6, 80.3, 75.1, 65.3, 61.5, 60.6, 43.0, 41.9, 28.4, 28.3, 25.3, 24.7, 23.5, 20.9, 19.2; IR (neat) 2983, 1694, 1681, 1210 cm$^{-1}$

Example 3 2-formylpiperidinium chloride

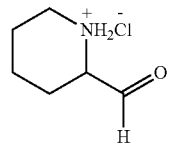

A solution of tert-butyl 2-formylpiperidine-1-carboxylate (1 kg, 4.7 mol) in IPAc (5 L) was added drop wise to a solution of HCl (0.17 kg, 9.4 mol) in IPAc (7 L) for 30 min at 0~5° C. The mixture was stirred for 30 min at 0~5° C. After reaction was complete, the resulting mixture was filtered. The precipitate was washed with IPAc (2 L) and dried under vacuum at 20~25° C. for 24 h. The precipitate was dried under vacuum at 20~25° C. for 24 h. 630 g of the product 2-formylpiperidinium chloride was obtained as a white powder. (Yield 90%) $^1$H-NMR (400 MHz, D$_2$O) δ ppm 4.95-5.09 (m, 1H), 3.29-3.44 (m, 1H), 2.85-3.06 (m, 2H), 1.73-2.04 (m, 3H), 1.37-1.66 (m, 3H); $^{13}$CNMR (100 MHz, D2O) δ ppm 88.6, 60.5, 44.6, 23.6, 21.9, 21.0; IR (Neat) 2939, 2720, 1525, 1448, 1344, 1250, 1124, 1082, 1053, 1021 cm$^{-1}$; LCMS, m/z 113.1 (131.1)

Example 4 tert-butyl 1-oxo-3,4,6,7,8,9-hexahydropyrido[3,4-b]indolizine-2(1H)-carboxylate

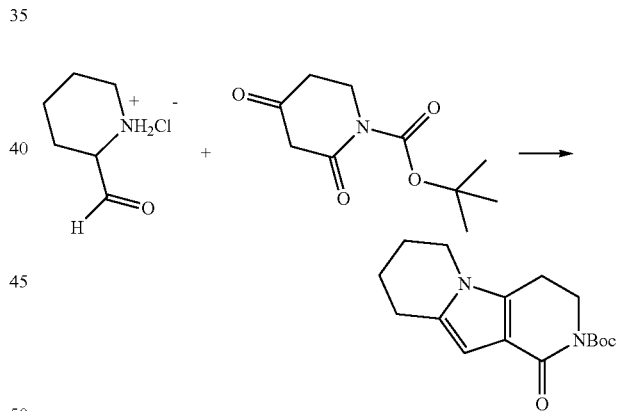

Tert-butyl 2,4-dioxopiperidine-1-carboxylate (CAS Reg. No. 845267-78-9), also named as 1-piperidinecarboxylic acid, 2,4-dioxo-1,1-dimethylethyl ester, is prepared from 2,4-Piperidinedione (CAS Reg. No. 50607-30-2) and Di-tert-butyl dicarbonate or the methods of Ferrer, Manel et al (2013) Tetrahedron Letters, 54(36):4821-4825; Tanaka et al (2011) Tetrahedron Letters, 52(39):5036-5038; EP 2526945; EP 2380890; WO 2012035078; WO 2012058193.

Tert-butyl 2,4-dioxopiperidine-1-carboxylate, (1 kg, 4.7 mol) was dissolved in DCM (15 L). 4 A molecular sieves (MS, 1.5 kg) was added. The mixture was cooled to 0~5° C. Pyrrolidine (1.4 kg, 19.7 mol) was added at 0~5° C. and stirred for 30 min. 2-formylpiperidinium chloride from Example 3 (1 kg, 6.6 mol) was added via portions at 0~5° C. for 2 h. The mixture was stirred for 2 hr at 0~5° C. The mixture was filtered. The filtrate was washed with water (2×10 L). The organic layer containing product tert-butyl 1-oxo-3,4,6,7,8,9-hexahydropyrido[3,4-b]indolizine-2(1H)-carboxylate was carried forward to the next step. (Assay yield 68%) H-NMR (400 MHz, CDCl$_3$) δ ppm 6.27 (br, 1H), 4.08 (t, 2H, J=6 Hz), 3.79 (t, 2H, J=6 Hz), 2.77 (t, 4H, J=6 Hz), 1.94-2.07 (m, 2H), 1.78-1.90 (m, 2H), 1.56 (s, 9H); $^{13}$CNMR (100 MHz, CDCl$_3$) δ ppm 162.9, 154.0, 136.4, 130.9, 114.2, 103.4, 82.1, 45.0, 43.1, 28.2, 23.4, 23.2, 21.4, 20.8; IR (Neat) 2941, 1698, 1684, 1486.35, 1457, 1417, 1396, 1370, 1333, 1316, 1269, 1256, 1158, 1140, 1100, 1044, 940, 857, 828, 776, 762, 715 cm$^{-1}$; LCMS, m/z 290.1 (235.0)

Example 5 3,4,6,7,8,9-hexahydropyrido[3,4-b]indolizin-1(2H)-one

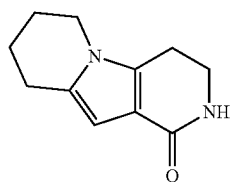 [SMILES: O=C1NCCc2c1cc1n2CCCC1]

Crude tert-butyl 1-oxo-3,4,6,7,8,9-hexahydropyrido[3,4-b]indolizine-2(1H)-carboxylate (starting with 1 kg of tert-butyl 2,4-dioxopiperidine-1-carboxylate) in DCM from Example 4 was cooled to 0~5° C. TFA (2.7 kg, 28 mol) was added dropwise at 0~5° C. and stirred for 2 h at 20~25° C. The mixture was washed with H$_2$O (2×10 L), 1 N HCl (5 L) and 7% NaHCO$_3$ (10 L). Precipitate was formed. The mixture was filtered and the organic layer was concentrated under vacuum. The resulting mixture was combined and refluxed in ethanol (1.5 L) for 5 h. The mixture was cooled to 20~25° C. naturally. The precipitate was filtered and washed with ethanol (0.5 L). After drying under vacuum at 40~45° C. for 24 h, 500 g of product 3,4,6,7,8,9-hexahydropyrido[3,4-b]indolizin-1(2H)-one was obtained as an off-white powder. (Yield 56%) $^1$HNMR (400 MHz, CDCl$_3$) δ ppm 6.22 (s, 1H), 5.59 (br, 1H), 3.80 (t, 2H, J=6 Hz), 3.57 (td, 2H, J$_1$=6 Hz, J$_2$=2 Hz), 2.72-2.81 (m, 4H), 1.92-2.02 (m, 2H), 1.77-1.86 (m, 2H); $^{13}$CNMR (100 MHz, CDCl$_3$) δ ppm 167.2, 134.5, 130.0, 113.1, 102.1, 43.1, 41.0, 23.5, 23.3, 21.0, 21.0

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

The invention claimed is:

1. A process for preparing a tricyclic lactam compound of Formula I, having the structure:

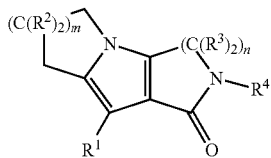

comprising reacting intermediates 1 and 2 to form I

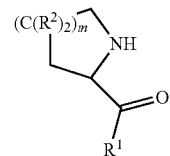

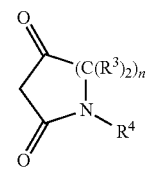

wherein R$^1$ is selected from H and C$_1$-C$_6$ alkyl;

R$^2$ is independently selected from H, F, Cl, C$_1$-C$_6$ alkyl, or phenyl;

R$^3$ are independently selected from H, F, Cl, C$_1$-C$_6$ alkyl, or phenyl;

R$^4$ is selected from H, tert-butyloxycarbonyl (Boc), benzyloxycarbonyl (CBz), allyloxycarbonyl (Alloc), or fluorenylmethyloxycarbonyl (Fmoc);

m is 1 or 2; and n is 1 or 2, where the tricyclic lactam compound of Formula I and intermediates 1 and 2 include all stereoisomers, geometric isomers, tautomers, and salts thereof.

2. The process of claim 1 wherein intermediate 1 is prepared by oxidation of alcohol intermediate 3:

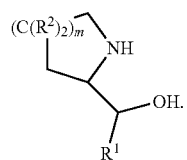

3. The process of claim 1 or 2 wherein intermediate 1 is prepared by a process comprising:

(a) reacting alcohol 3 with a protection reagent to form N-protected intermediate 4

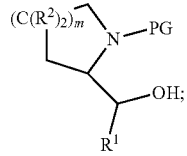

(b) oxidation of 4 to form oxidized N-protected intermediate 5

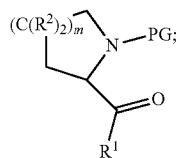

and (c) deprotection of 5 to form 1, where PG is tert-butyloxycarbonyl (Boc), benzyloxycarbonyl (CBz), allyloxycarbonyl (Alloc), or fluorenylmethyloxycarbonyl (Fmoc).

4. The process of claim 3 wherein PG is tert-butyloxycarbonyl (Boc).

5. The process of claim 1 wherein $R^1$ is H.

6. The process of claim 1 wherein $R^4$ is tert-butyloxycarbonyl (Boc).

7. The process of claim 1 wherein m is 1.

8. The process of claim 1 wherein m is 2.

9. The process of claim 8 wherein m is 2, n is 2, and each $R^2$ and $R^3$ is H.

10. The process of claim 1 wherein intermediate 1 is a salt.

11. The process of claim 1 further comprising adding pyrrolidine to the reaction of intermediates 1 and 2.

12. The process of claim 1 further comprising adding trifluoroacetic acid after the reaction of intermediates 1 and 2 whereby the tricyclic lactam compound of Formula I where $R^4$ is H is formed.

13. The process of claim 1 wherein intermediate 1 is piperidine-2-carbaldehyde hydrochloride.

14. The process of claim 1 wherein intermediate 2 is tert-butyl 2,4-dioxopiperidine-1-carboxylate.

15. The process of claim 1 wherein the tricyclic lactam compound of Formula I is 3,4,6,7,8,9-hexahydropyrido[3,4-b]indolizin-1(2H)-one.

* * * * *